US009456909B2

(12) United States Patent
Johnson et al.

(10) Patent No.: US 9,456,909 B2
(45) Date of Patent: Oct. 4, 2016

(54) MODULAR LIMB SEGMENT CONNECTOR

(71) Applicants: Ezra Johnson, Fredericksburg, VA (US); W. Travis Lontz, Fredericksburg, VA (US); Thomas W. Van Doren, Fredericksburg, VA (US)

(72) Inventors: Ezra Johnson, Fredericksburg, VA (US); W. Travis Lontz, Fredericksburg, VA (US); Thomas W. Van Doren, Fredericksburg, VA (US)

(73) Assignee: HDT Expeditionary Systems, Inc., Solon, OH (US)

( * ) Notice: Subject to any disclaimer, the term of this patent is extended or adjusted under 35 U.S.C. 154(b) by 64 days.

(21) Appl. No.: 13/664,990
(22) Filed: Oct. 31, 2012

(65) Prior Publication Data

US 2013/0059467 A1 Mar. 7, 2013

Related U.S. Application Data

(62) Division of application No. 12/959,816, filed on Dec. 3, 2010, now Pat. No. 8,425,620.

(60) Provisional application No. 61/267,629, filed on Dec. 8, 2009.

(51) Int. Cl.
*A61F 2/50* (2006.01)
*A61F 2/58* (2006.01)
(Continued)

(52) U.S. Cl.
CPC .............. *A61F 2/76* (2013.01); *A61F 2/585* (2013.01); *B25J 15/04* (2013.01); *B25J 19/0029* (2013.01);
(Continued)

(58) Field of Classification Search
CPC ............ A61F 2/70; A61F 2/78; A61F 2/581; A61F 2/582; A61F 2/585; A61F 2/54; A61F 2/58; A61F 2/583; A61F 2/76; A61F 2002/5003; A61F 2002/5007; A61F 2002/5009; A61F 2002/543; A61F 2009/546; A61F 2002/5072; A61F 5002/5073; A61F 2002/5078; A61F 2002/5079

USPC .............. 623/25, 27, 31–33, 38, 57, 59–60, 623/62–645; 403/353, 376; 74/490.02, 74/490.06, 490.2
See application file for complete search history.

(56) References Cited

U.S. PATENT DOCUMENTS 4,512,709 A 4/1985 Hennekes et al.
4,521,924 A 6/1985 Jacobsen et al.
(Continued)

FOREIGN PATENT DOCUMENTS

DE 103 26 239 1/2005
EP 0 081 299 A2 6/1983
(Continued)

OTHER PUBLICATIONS

Murata, Satoshi et al., "Hardware Design of Modular Robotic Systems", Proc. of 2000 IEEE/RSJ Int. Conf. on Intelligent Robots and Systems (IROS 2000), CD-ROM, F-AIII-5, 2000, 8 pages.
(Continued)

*Primary Examiner* — Thomas J Sweet
*Assistant Examiner* — Christie Bahena
(74) *Attorney, Agent, or Firm* — Fay Sharpe LLP

(57) ABSTRACT

A joint assembly for releasably securing a first and a second segment of an associated modular limb is provided. The joint assembly includes a male connector including a base and a load bearing blade secured to the base of the male connector protruding therefrom. The male connector is adapted to be secured to one of the first and second segments of the associated modular limb. A female connector is provided and includes a base and a load bearing socket secured to the base of the female connector. The socket is configured to selectively receive the blade of the male connector. The female connector is adapted to be secured to the other of the first and second segments of the associated modular limb. A locking member selectively retains the blade of the male connector in the socket of the female connector. The male connector, the female connector, and the locking member cooperate to form a resilient and selectively releasable modular limb joint.

19 Claims, 15 Drawing Sheets

(51) Int. Cl.
*A61F 2/68* (2006.01)
*A61F 2/70* (2006.01)
*A61F 2/76* (2006.01)
*B25J 15/04* (2006.01)
*B25J 19/00* (2006.01)

(52) U.S. Cl.
CPC .......... *A61F 2/70* (2013.01); *A61F 2002/5007* (2013.01); *A61F 2002/5083* (2013.01); *A61F 2002/6854* (2013.01); *A61F 2002/7645* (2013.01); *Y10T 74/20335* (2015.01); *Y10T 403/7075* (2015.01)

(56) References Cited

U.S. PATENT DOCUMENTS

| | | | |
|---|---|---|---|
| 4,766,775 A * | 8/1988 | Hodge | 74/490.01 |
| 4,905,938 A * | 3/1990 | Braccio et al. | 244/101 |
| 5,523,662 A * | 6/1996 | Goldenberg et al. | 318/568.11 |
| 5,712,552 A | 1/1998 | Hirai et al. | |
| 5,800,563 A | 9/1998 | Arbogast et al. | |
| 5,910,720 A | 6/1999 | Williamson et al. | |
| 6,323,615 B1 | 11/2001 | Khairallah | |
| 6,454,624 B1 | 9/2002 | Duff et al. | |
| 6,491,537 B1 | 12/2002 | Watanabe | |
| 6,575,802 B2 | 6/2003 | Yim et al. | |
| 6,605,914 B2 | 8/2003 | Yim et al. | |
| 6,686,717 B2 | 2/2004 | Khairallah | |
| 6,780,042 B1 | 8/2004 | Badescu et al. | |
| 6,791,291 B2 | 9/2004 | Shimizu et al. | |
| 7,296,835 B2 | 11/2007 | Blackwell et al. | |
| 7,549,883 B2 | 6/2009 | Hillis et al. | |
| 8,591,599 B1 * | 11/2013 | Kaliki et al. | 623/25 |
| 8,601,667 B2 * | 12/2013 | Norton | 29/428 |
| 8,690,963 B2 * | 4/2014 | Puchhammer | 623/61 |
| 2005/0049720 A1 * | 3/2005 | Benson | 623/38 |
| 2005/0267600 A1 | 12/2005 | Haberman et al. | |
| 2006/0079965 A1 * | 4/2006 | Benson | 623/38 |
| 2007/0021841 A1 * | 1/2007 | Al-Temen et al. | 623/25 |
| 2007/0228671 A1 * | 10/2007 | Norton | 279/2.11 |
| 2008/0129239 A1 | 6/2008 | Lee et al. | |
| 2008/0276725 A1 * | 11/2008 | Pusch | 73/862.041 |
| 2008/0288088 A1 * | 11/2008 | Langenfeld et al. | 623/57 |
| 2009/0192619 A1 | 7/2009 | Martin et al. | |
| 2010/0016990 A1 * | 1/2010 | Kurtz | 623/24 |

FOREIGN PATENT DOCUMENTS

| | | | | |
|---|---|---|---|---|
| EP | 0 441 397 | | 8/1991 | |
| GB | 2236054 A | * | 3/1991 | A61F 2/58 |

OTHER PUBLICATIONS

Yim, Mark et al., "Towards Robotic Self-Reassembly After Explosion", 2007, 7 pages.
Yim, Mark et al., "Modular Self-Reconfigurable Robot Systems, Challenges and Opportunities for the Future", IEEE Robotics & Automation Magazine, Mar. 2007, pp. 43-52.
Yim, Mark et al., "Modular Reconfigurable Robots in Space Applications", Autonomous Robots, 14, 2003, pp. 225-237.
Salemi, Behnam et al., "SUPERBOT: A Deployable, Multi-Functional, and Modular Self-Reconfigurable Robotic System", Proceedings of the 2006 IEEE/RSJ International Conference on Intelligent Robots and Systems, Oct. 9-15, 2006, Beijing, China, pp. 3636-3641.
Chiang, Chih-Jung et al., "Modular Robot Motion Planning Using Similarity Metrics", Autonomous Robots, 10, 2001, pp. 91-106.
Jantapremjit, Pakpong, et al., "Design of a Modular Self-Reconfigurable Robot", Robotic Systems Laboratory, The Australian National University, Canberra, Australia, 6 pages.
Jorgensen, Morten Winkler, et al., "Modular ATRON: Modules for a Self-Reconfigurable Robot", Proceedings of 2004 IEEE/RSJ International Conference on Intelligent Robots and Systems, Sep. 28-Oct. 2, 2004, Sendai, Japan, pp. 2068-2073.
Khoshnevis, Behrokh et al., "Reconnectable Joints for Self-Reconfigurable Robots", Information Sciences Institute, Marina del Rey, California and Department of Industrial and Systems Engineering, University of Southern California, Los Angeles, California, 6 pages.
Duff, David G. et al., "Evolution of PolyBot: A Modular Reconfigurable Robot", Palo Alto, California, 7 pages.
Yim, Mark et al., "Modular Robots", IEEE Spectrum, Feb. 2002, pp. 30-34.
http://www.oandp.org./jpo/library/printArticle.asp?printArticleId= 2 . . . , Journal of Prosthetics and Orthotics 2007, "The ToMPAW Modular Prosthesis: A Platform for Research in Upper-Limb Prosthetics", vol. 19, Num. 1, p. 15 (8 pages).
http://www.jhuapl.edu/newscenter/pressreleases/2007/070426.asp, The Johns Hopkins University Applied Physics Laboratory, "Revolutionizing Prosthetics 2009 Team Delivers First DARPA Limb Prototype", Apr. 26, 2007 (3 pages).
http://www.medicalnewstoday.com/printerfriendlynews. php?newsid . . . , Medical News Today, "Revolutionizing Prosthetics 2009 Team Delivers First DARPA Limb Prototype", May 2, 2007 (3 pages).
Beard, Jonathan, *50 Years of Bridging the Gap*, "Darpa's Bio-Revolution", DARPA pp. 155-161, Circa Apr. 2008.
Harshbarger, Stuart, The John Hopkins University Applied Physics Laboratory, Powerpoint Presentation, "Revolutionizing Prosthetics 2009", Dec. 2006 (19 pages).
Castano, Andres et al., "Mechanical Design of a Module for Reconfigurable Robots", Proceedings of the 2000 IEEE/RSJ International Conference on Intelligent Robots and Systems, 2000, pp. 2203-2209.
Invitation to Pay Additional Fees with Partial International Search Report of International Application No. PCT/US2010/059229 dated Mar. 23, 2011 (5 pages).
International Search Report of International Application No. PCT/US2010/059229 dated May 26, 2011 (8 pages).
Written Opinion of International Application No. PCT/US2010/059229 dated May 26, 2011 (9 pages).
International Preliminary Report on Patentability/Written Opinion of the International Searching Authority of International Application No. PCT/US2010/059229 dated Jun. 21, 2012.

* cited by examiner

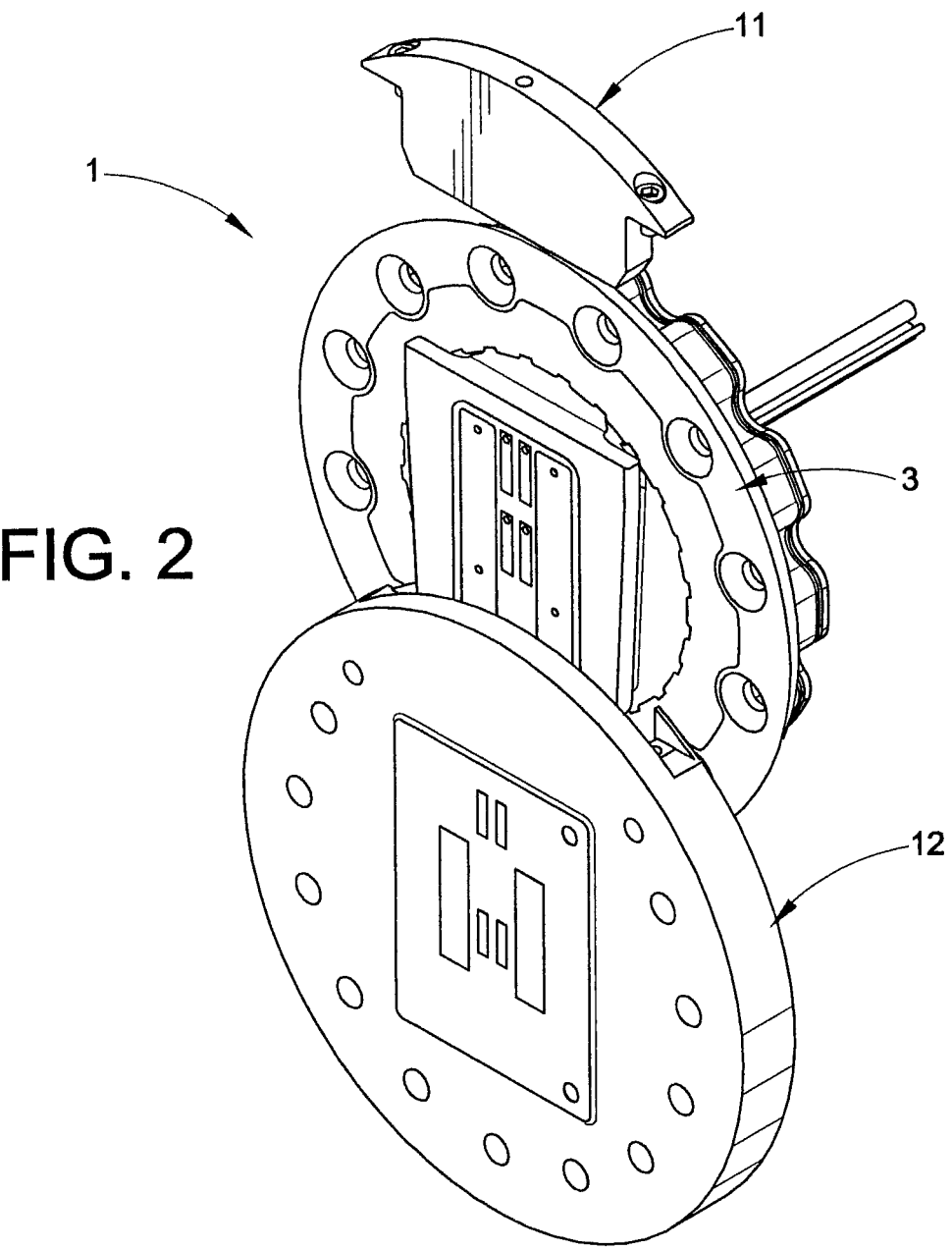

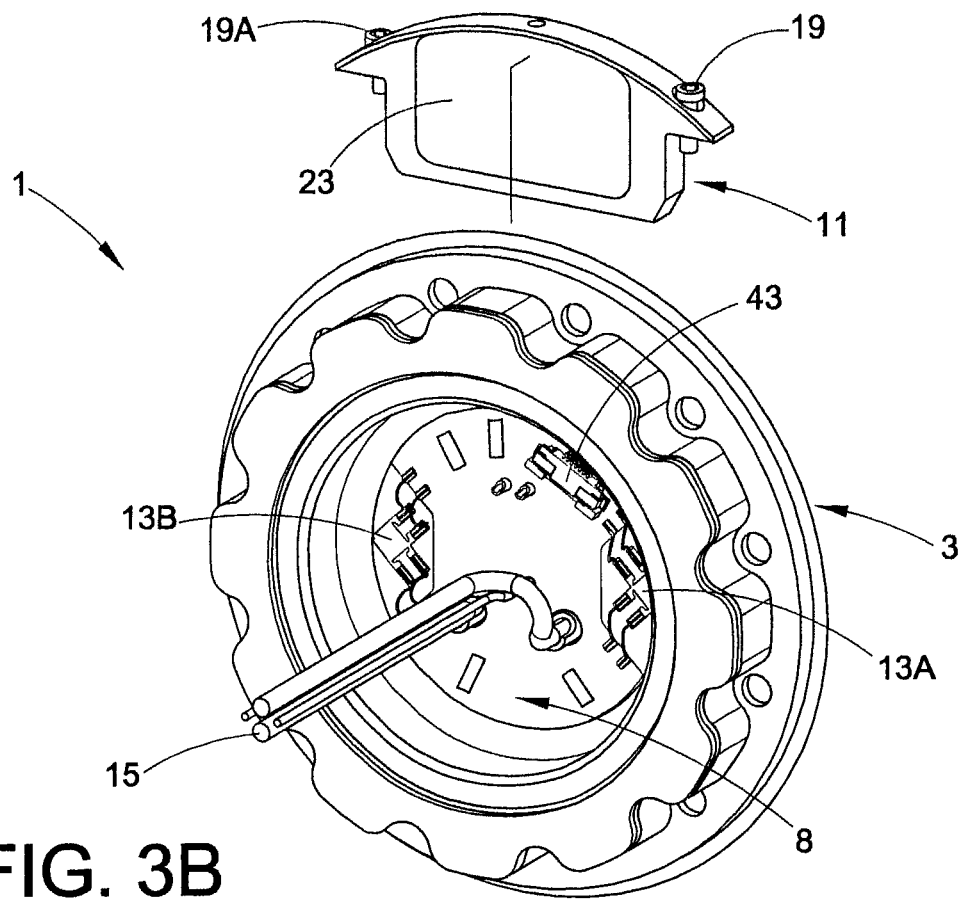
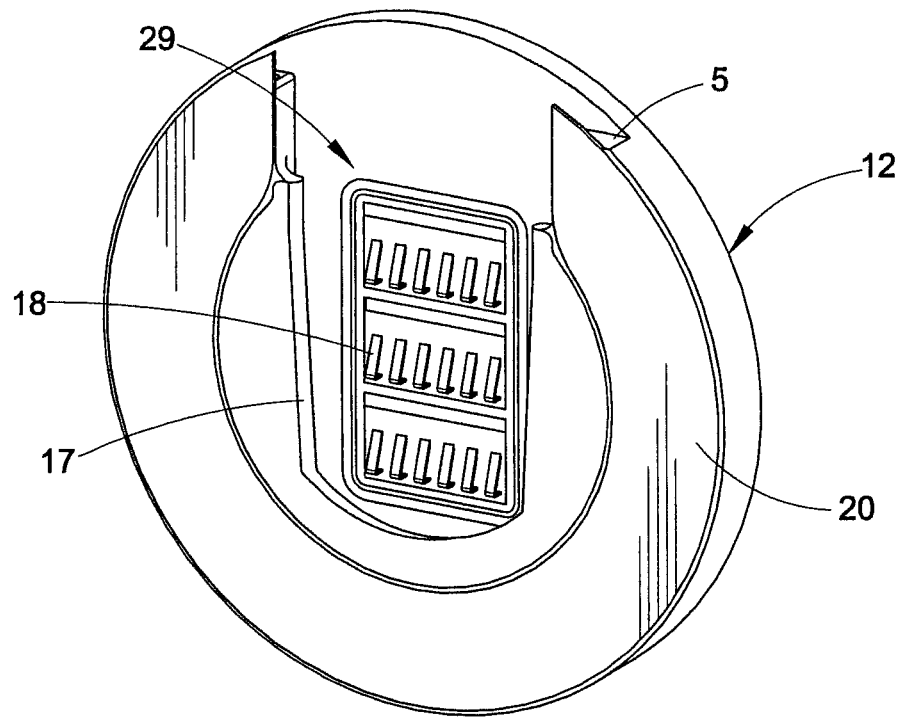
FIG. 3B

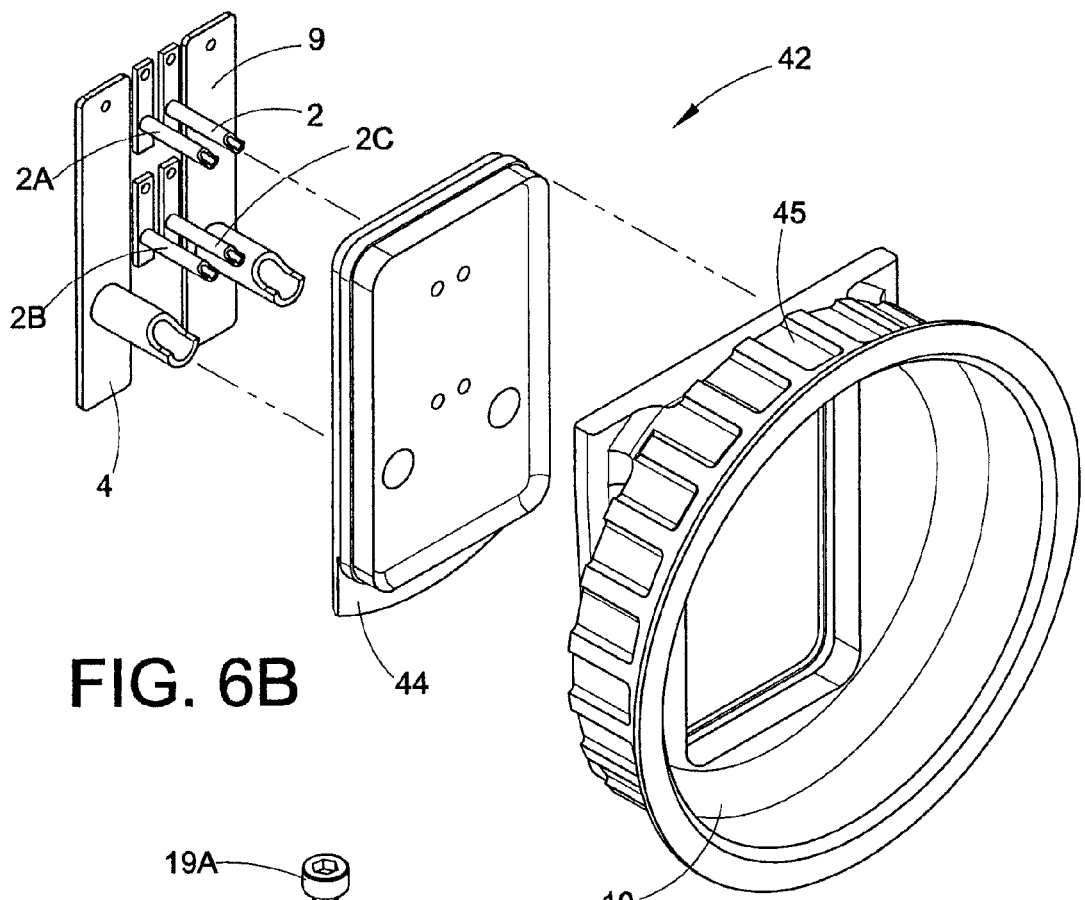
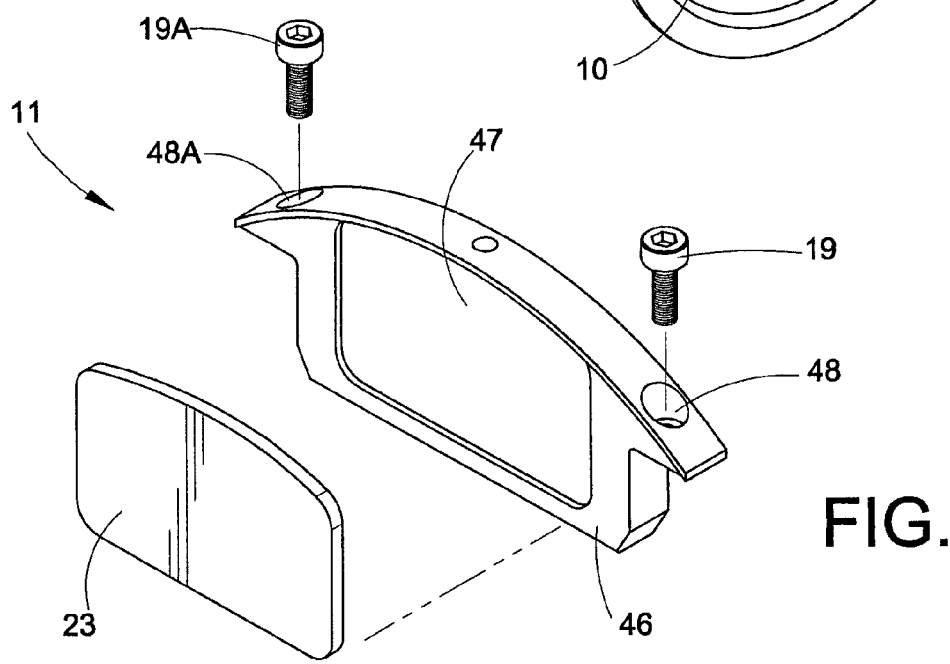
FIG. 6B
FIG. 7

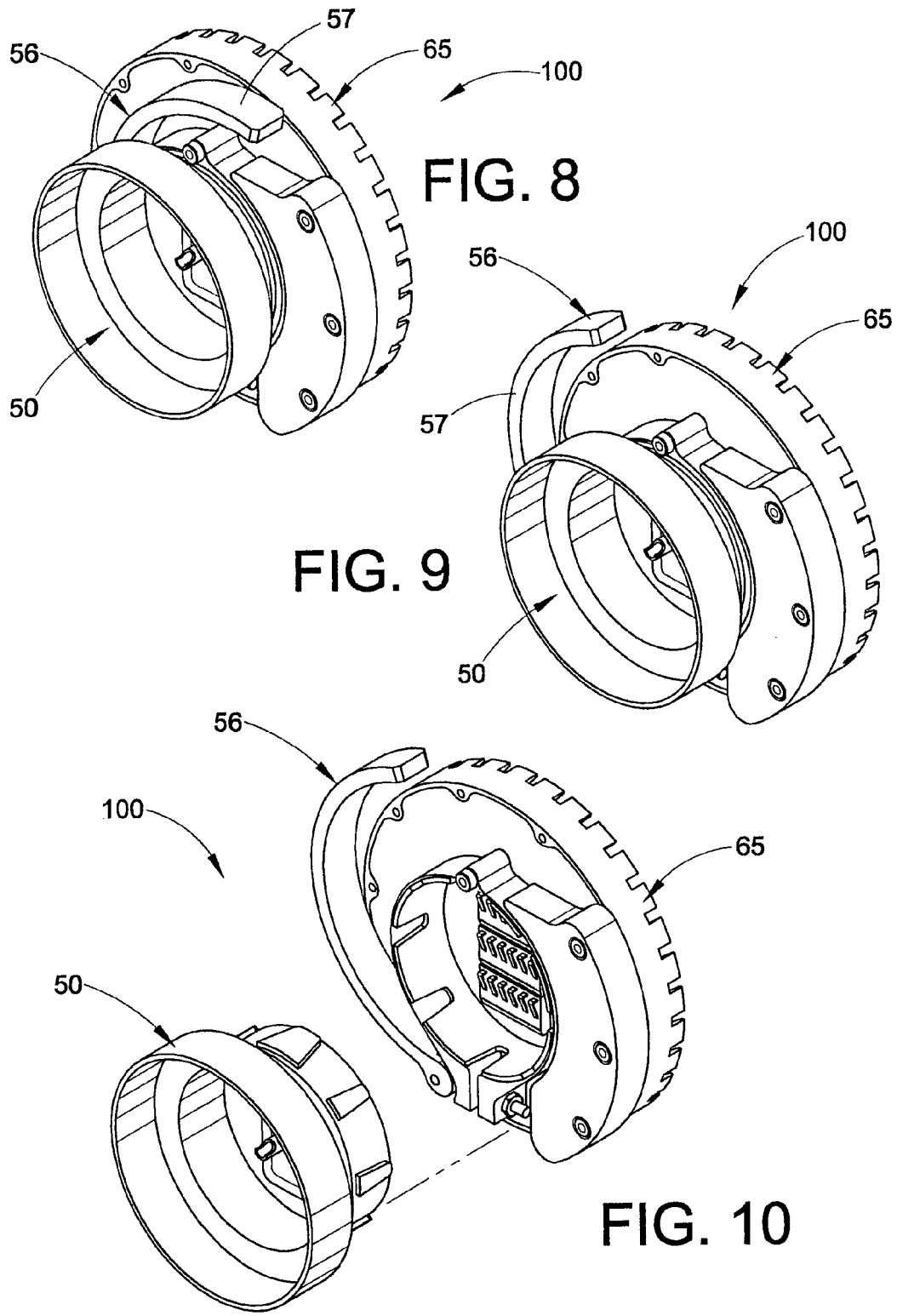

MODULAR LIMB SEGMENT CONNECTOR

This application is a division of application Ser. No. 12/959,816 which was filed on Dec. 3, 2010 and is still pending. That application in turn claims priority from U.S. Provisional Application Ser. No. 61/267,629 which was filed on Dec. 8, 2009 and the entire disclosure of which is incorporated herein by reference.

BACKGROUND

The present disclosure relates to man-made or artificial limbs for prosthetic or orthotic devices, as well as for robots. More particularly, it relates to a modular limb segment connector, such as an arm segment connector, which can be used in prosthetics, as well as for robotics applications when an artificial limb is required.

In the field of prosthetics, there remains a limited ability to control prosthetic and/or orthotic joints in a suitable manner for practical clinical application. While great strides have been made in prosthetic legs, the development of prosthetic arms has not been as advanced. Typically, limbs such as arms, whether for prosthetics or robotics, are assembled with custom bolted and screwed mechanical connections that are different for each joint. These mechanical connections may or may not include the electrical interconnections between adjacent arm components. Typical solutions can include complex wiring harnesses that require bulky electrical connectors or solder connections. Such solutions are disadvantageous because they only work for a specific joint. In other words, they are not usable for joints between multiple arm modules.

Although prosthetic technology has advanced in recent years, the prior art still has failed to bridge the gap between manmade prosthetics and user demands and needs. Therefore, an extensive opportunity for design advancements and innovation remains where the prior art fails or is deficient. Most myoelectric prosthetic arms move in three ways. They bend at the elbow, rotate at the wrist and a rudimentary hand clamps shut. A need exists to replicate the great many varieties of movements that a human arm is capable of making. It is believed that a human arm has 27 degrees of freedom, including individual finger bending, and the use of an opposable thumb. Robotic arms used as prostheses are not fully articulated to give the user the same degrees of freedom as a natural arm, not to mention the speed and torque of a human arm. Moreover, the human arm can sense pressure, which conventional man-made arms cannot do. It would be advantageous if the prosthetic or robotic arm was sensitive enough to pick up a piece of paper, a wine glass or even a grape without mishap.

While many advances are taking place to allow for better prosthetics and orthotics, as well as more functional robotic limbs, there remains a need to develop better connections for the various segments of a limb so that the segments can be more readily attached and detached in a simple manner, without external wiring, and in a manner that provides a weather tight seal. It would also be advantageous to provide sensors for torque being transmitted between adjacent components of a limb.

BRIEF DISCLOSURE OF THE DEVELOPMENT

According to one aspect of the present disclosure, a joint assembly for releasably securing a first and a second segment of an associated modular limb is provided. The joint assembly includes a male connector including a base and a load bearing blade secured to the base of the male connector protruding therefrom. The male connector is adapted to be secured to one of the first and second segments of the associated modular limb. A female connector is provided and includes a base and a load bearing socket secured to the base of the female connector. The socket is configured to selectively receive the blade of the male connector. The female connector is adapted to be secured to the other of the first and second segments of the associated modular limb. A locking member selectively retains the blade of the male connector in the socket of the female connector. The male connector, the female connector, and the locking member cooperate to form a resilient and selectively releasable modular limb joint.

According to another aspect of the present disclosure, another joint assembly for releasably securing a first and a second segment of an associated modular limb is provided. The joint assembly includes a male connector including a base, a load bearing hub secured to the base of the male connector, and at least one first electrical contact secured to the load bearing hub. The base of the male connector is adapted to be secured to one of the first and second segments of the associated modular limb. A female connector is provided including a base, a load bearing socket secured to the base of the female connector, and at least one second electrical contact secured to the load bearing socket. The socket is configured to selectively receive the hub of the male connector and the base of the female connector is adapted to be secured to the other of the first and second segments of the associated modular limb. The at least one first electrical contact is aligned with the at least one second electrical contact when the hub is received in the socket for establishing electrical communication between the first and second segments of the associated modular limb. The male connector and the female connector cooperate to form a resilient yet releasable modular limb joint.

According to yet another aspect of the present disclosure, a torque sensing quick-release joint assembly is provided for selectively securing a first segment of an associated artificial limb to a second segment thereof and sensing a torque transmitted therebetween. The joint assembly includes a male connector including a base and a load bearing projection secured to the base of the male connector. The base of the male connector is adapted to be secured to one of the first and second segments of the associated artificial limb. A female connector includes a base and a load bearing socket secured to the base of the female connector. The socket is configured to selectively receive the projection of the male connector. The base of the female connector is adapted to be secured to the other of the first and second segments of the associated artificial limb. A load sensor is secured to one of the male and female connectors for measuring a torsional load transmitted through the joint assembly. The male connector and the female connector cooperate to form a resilient yet releasable artificial limb joint.

BRIEF DESCRIPTION OF THE DRAWINGS

FIG. 2 shows a partially disassembled connector of FIG. 1A with a locking clip removed and male and female connector sides partially removed from each other.

FIGS. 3A and 3B show the connector of FIG. 2 in a fully disassembled condition.

FIGS. 6A and 6B show exploded views of the blade and electrical contact assembly of the male side of the connector of FIG. 2.

FIG. 7 shows an exploded view of the locking clip assembly of the connector of FIG. 2.

FIG. 8 shows a fully engaged and clamped connector according to a second embodiment of the present disclosure.

FIG. 9 shows the connector of FIG. 8 with a locking lever open.

FIG. 10 shows the connector of FIG. 8 with the locking lever open and male and female sides disengaged.

DETAILED DESCRIPTION OF THE FIRST EMBODIMENT

Figure 1A:
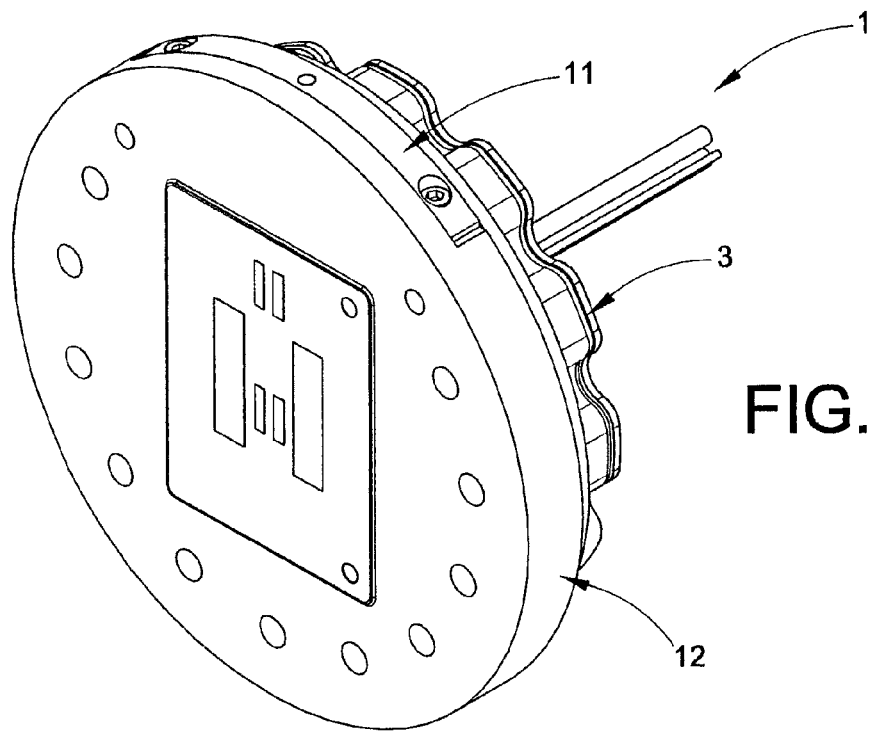
FIGS. 1A and 1B show a fully assembled and mated connector according to a first embodiment of the present disclosure.

One embodiment of the connector or modular joint assembly 1 for an artificial limb is shown in FIGS. 1A through 7. As is shown in the drawings and particularly in FIG. 2, the joint assembly includes a male side connector 3 which slides into a female side connector 12. A locking member or clip assembly 11 secures the two sides of the connector. The male connector, female connector, and locking member cooperate to form the resilient yet selectively releasable modular limb joint 1.

Figure 1B:
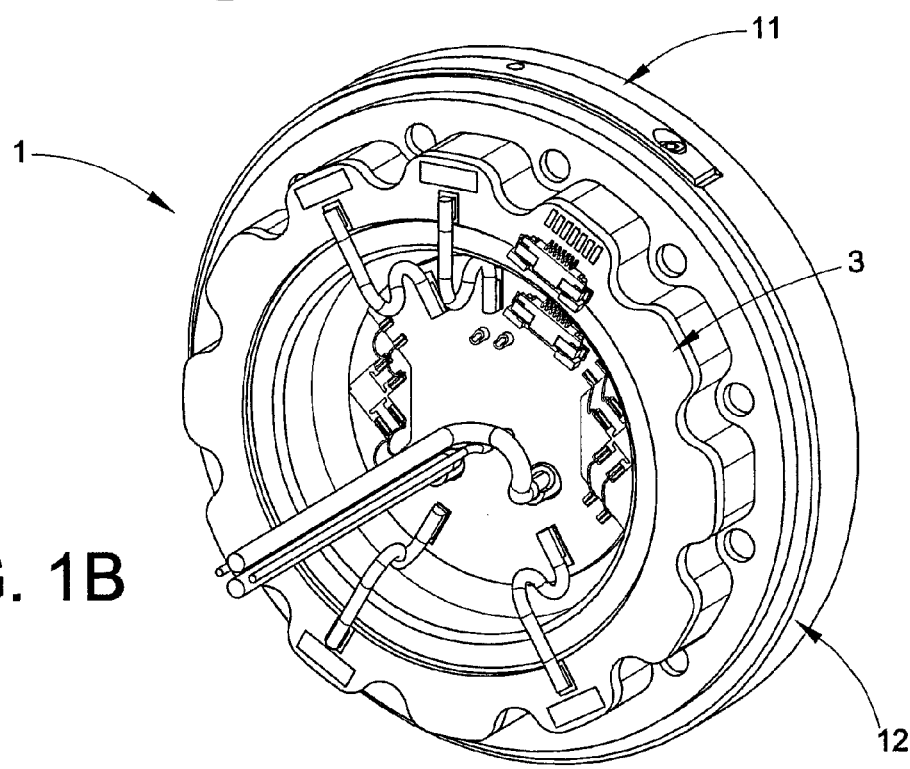
Figure 3A:
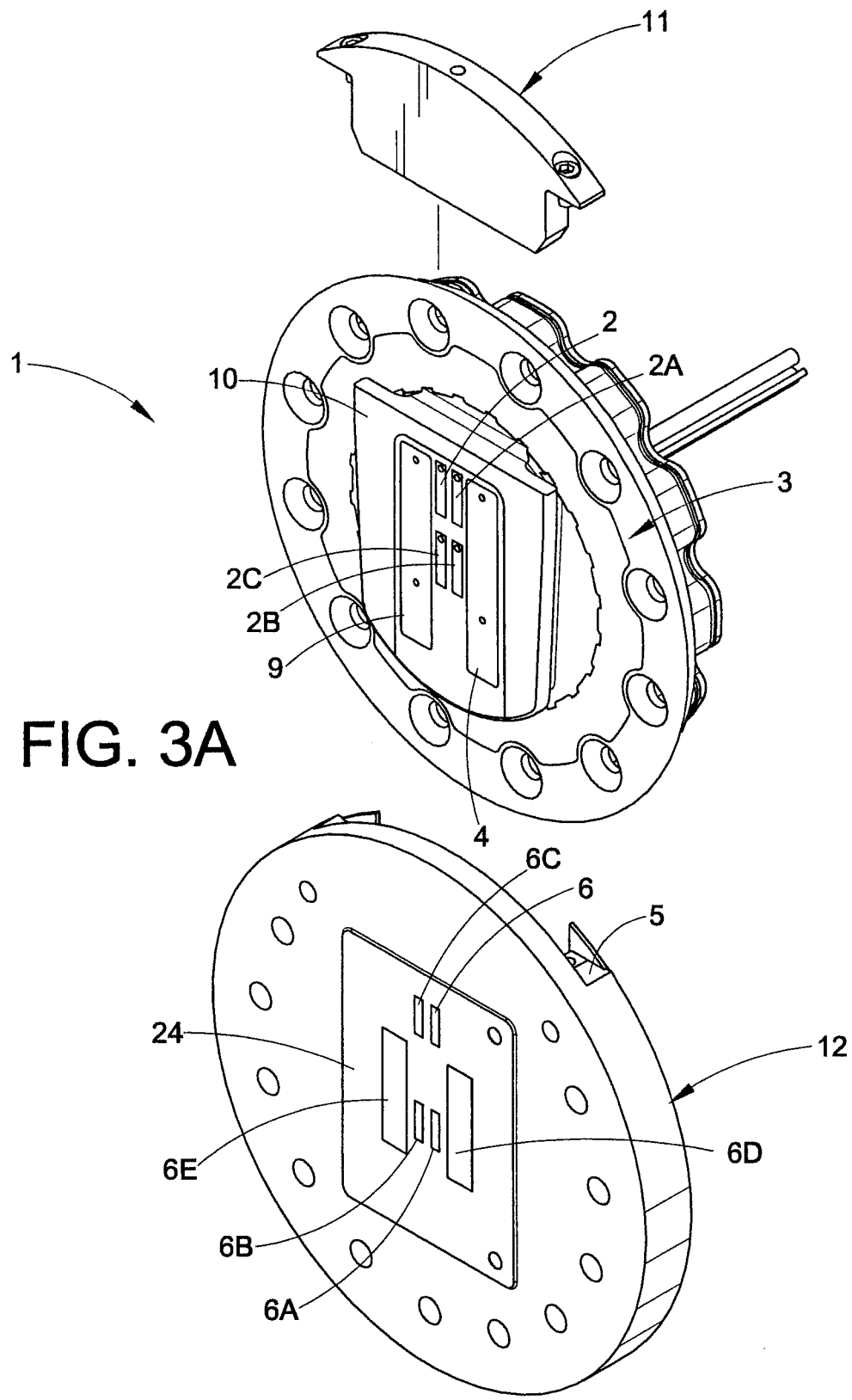

When fully assembled, in the embodiment shown in FIGS. 1A and 1B, the joint assembly 1 forms a compact assembly that provides robust mechanical attachment, multiple weather-sealed electrical connections, and integral torque sensing. As is shown in particular in FIGS. 3A and 3B, the mechanical attachment between the female side connector 12 and male side connector 3 is achieved when blade 10 or other load bearing projection of the male side connector assembly slides into a socket 29 or other receiver in the female connector 12. In particular, FIG. 3B shows that a U-shaped socket 29 is defined in the female side assembly 12 for this purpose. In the instant embodiment, blade 10 is received into or under the lip 17 in the socket 29. Electrical contact or communication through the joint can be achieved via one or more flat contacts 2, 2A, 2B, 2C, 4, and 9 in the male connector 3 which engage suitable elements in the female connector 12. By way of example only, electrical communication is established when the plurality of spring pins 18 (see FIG. 4B) in the female side connector 12 are seated against the contacts in the male connector as would typically occur upon full insertion of the blade 10 into the socket 29. Also, a pocket 5 (FIG. 3B) is formed above the socket 29 for receiving the locking clip assembly 11 once the male and female connectors are fully joined or engaged.

A unique feature of the instant disclosure is the ability of the modular limb joint assembly to sense torque, load, and/or pressure, etc. about the cylindrical axis of the connector assembly (or the axis of rotation of the joint). This can be measured by means of strain gages 13A and 13B and a strain gage signal conditioning circuit board 8 (FIGS. 3B, 5A and 5B) mounted to the back of the male blade 10. One or more electrical connectors 43 can be used for maintaining electrical communication to the conditioning circuit board 8, strain gages 13A, 13B, and/or other electronics through the various components of the limb, joint assembly, or individual male/female connectors. It should be noted that the strain gages 13A, 13B could include a full, half, or quarter strain gage bridge.

While the use of strain gages is illustrated in the instant disclosure, other torque or load sensing devices can be used such as load cells, piezoelectric sensors, or pressure/strain sensing semiconductors, etc. In addition, position sensors could be used to measure the relative rotational displacement between the male/female connectors of the joint which can then be used to calculate the associated torque and/or load values.

Such torque or load sensing capability is advantageous for a number of reasons. For one, it allows for a modular limb controller to properly limit the stresses that the joint and limb are subject to thereby preventing damage to the joint and/or limb. In addition, such load and/or torque information can be used by the controller to more accurately control limb motion, position, and/or to provide bio-feedback control, sensation, etc. for prosthetic limb users. An additional advantage is that torque or load sensing allows precise control of forces being exerted by the prosthetic limb on external objects (or people), thus preventing damage or injury to those objects or people. Furthermore, precise force control further enhances the stability of the system and/or limb as well as the stability of the objects being manipulated. Moreover, torque and/or load sensing is also advantageous for controlling the impedance of each joint for the same reasons that force or torque control is.

Figure 4A:
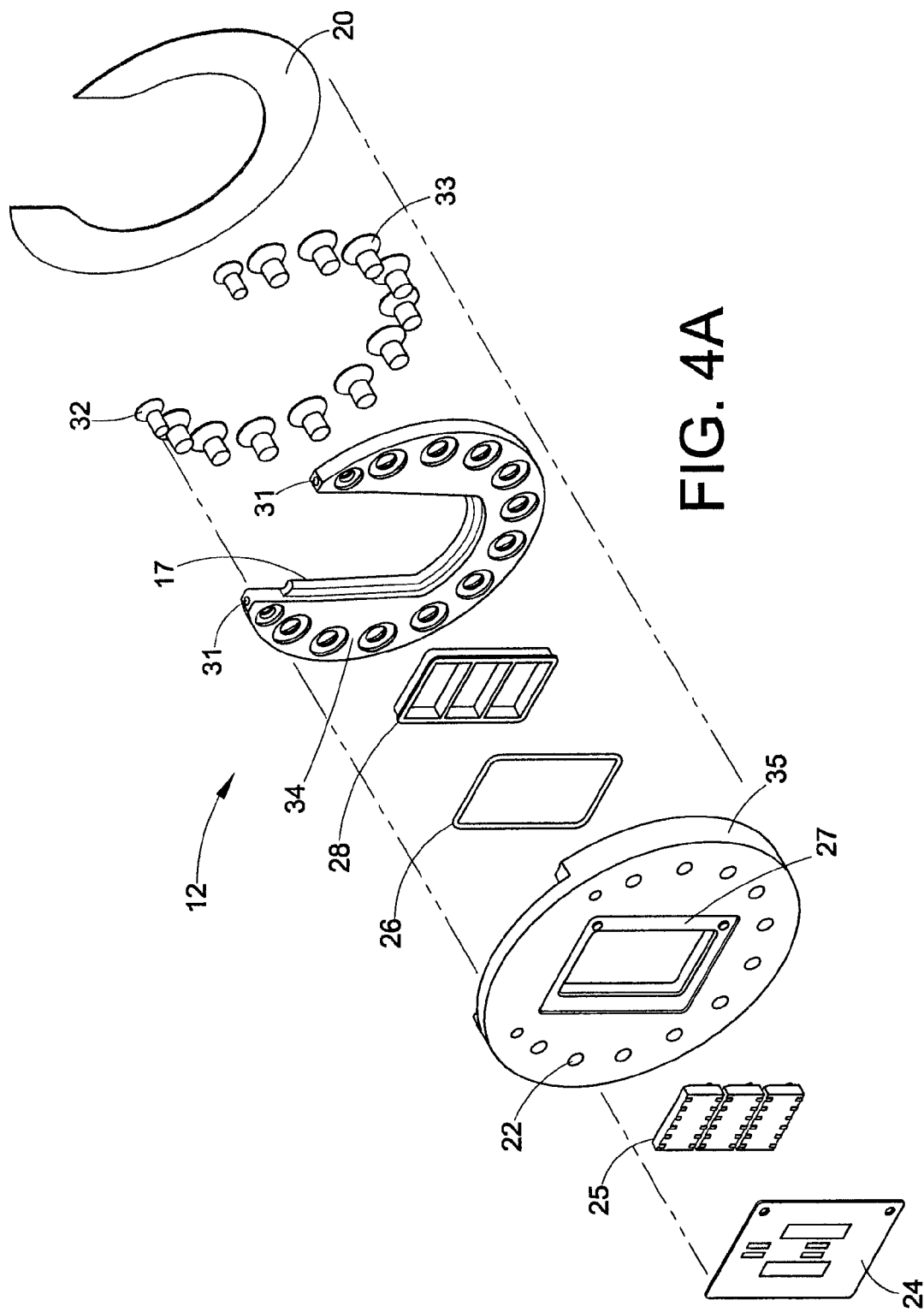
FIGS. 4A and 4B show exploded views of the female side of the connector of FIG. 2.
Figure 4B:
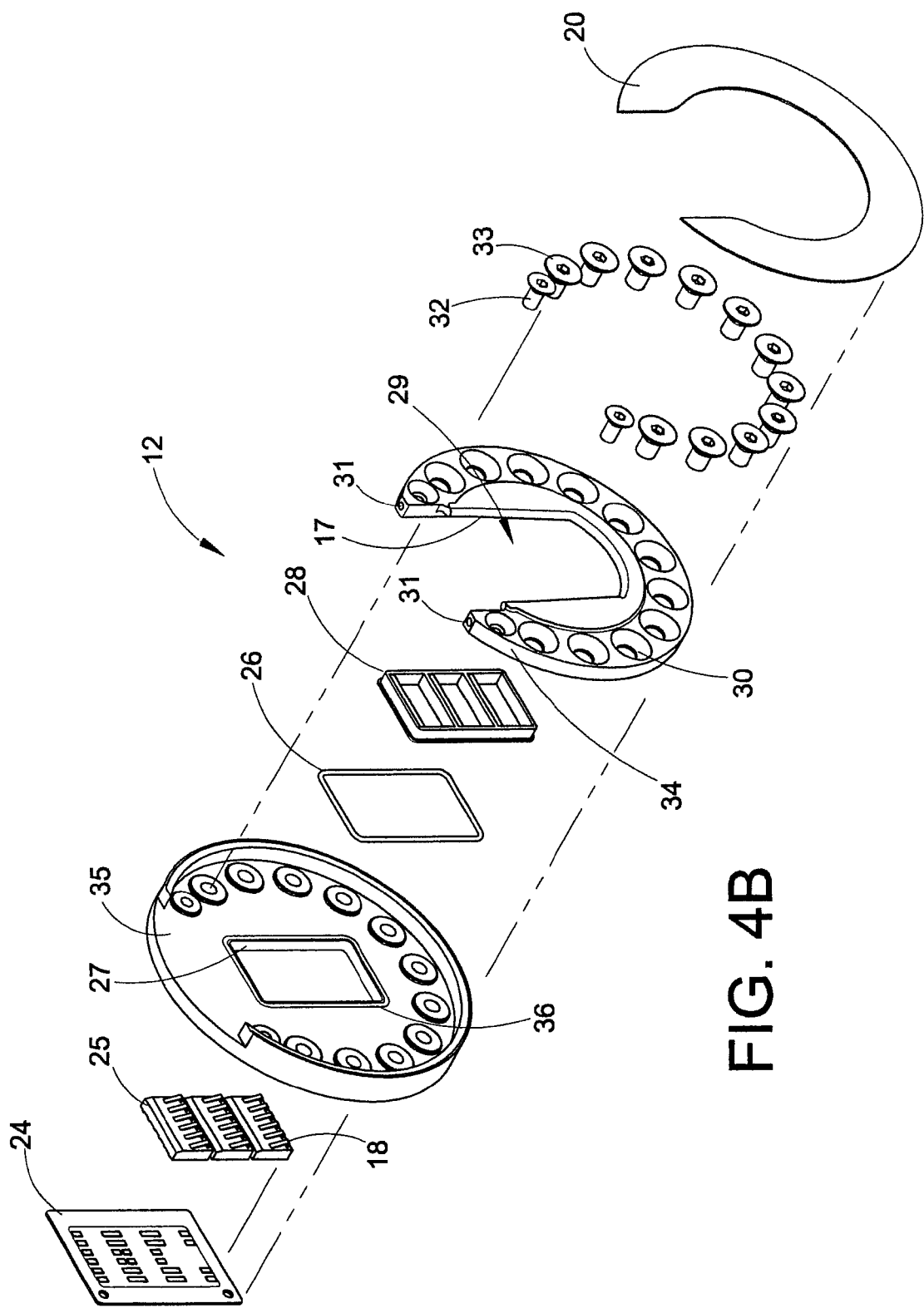

As is shown in the exploded views in FIGS. 4A and 4B, the female side connector/assembly 12 may include a spring pin mounting circuit board 24 having electrical contacts 6, 6A, 6B, 6C, 6D, and 6E (FIG. 3A), electrical spring pins 18 in spring pin blocks 25 (which are in electrical communication with contacts 6-6E), a socket or receiver plate 34, a connection backing 35, an o-ring 26, an electrical contact insulating member 28, and a connection plain bearing 20. As illustrated in FIGS. 4A and 4B, the spring pin circuit board 24 supports the spring pin blocks 25 which are both seated or received in a recess 27 of the connection backing 35. The insulating member 28 and the o-ring 26 are generally secured to either the spring pin circuit board 24, the spring blocks 25, and/or the connection backing 35. A plurality of screws 32, 33 can then be used to fasten together the socket or receiver plate 34 and the connection backing 35 (via holes 30, 22) to a respective modular limb segment. Once assembled, the socket or female receiver 29 is formed between the lip 17 of the socket plate 34 and the connection backing 35. Power and ground contacts 4 and 9 of the male joint connector 12 can each be contacted by multiple spring pins 18 to allow high electrical currents to flow across the joint.

Figure 5A:
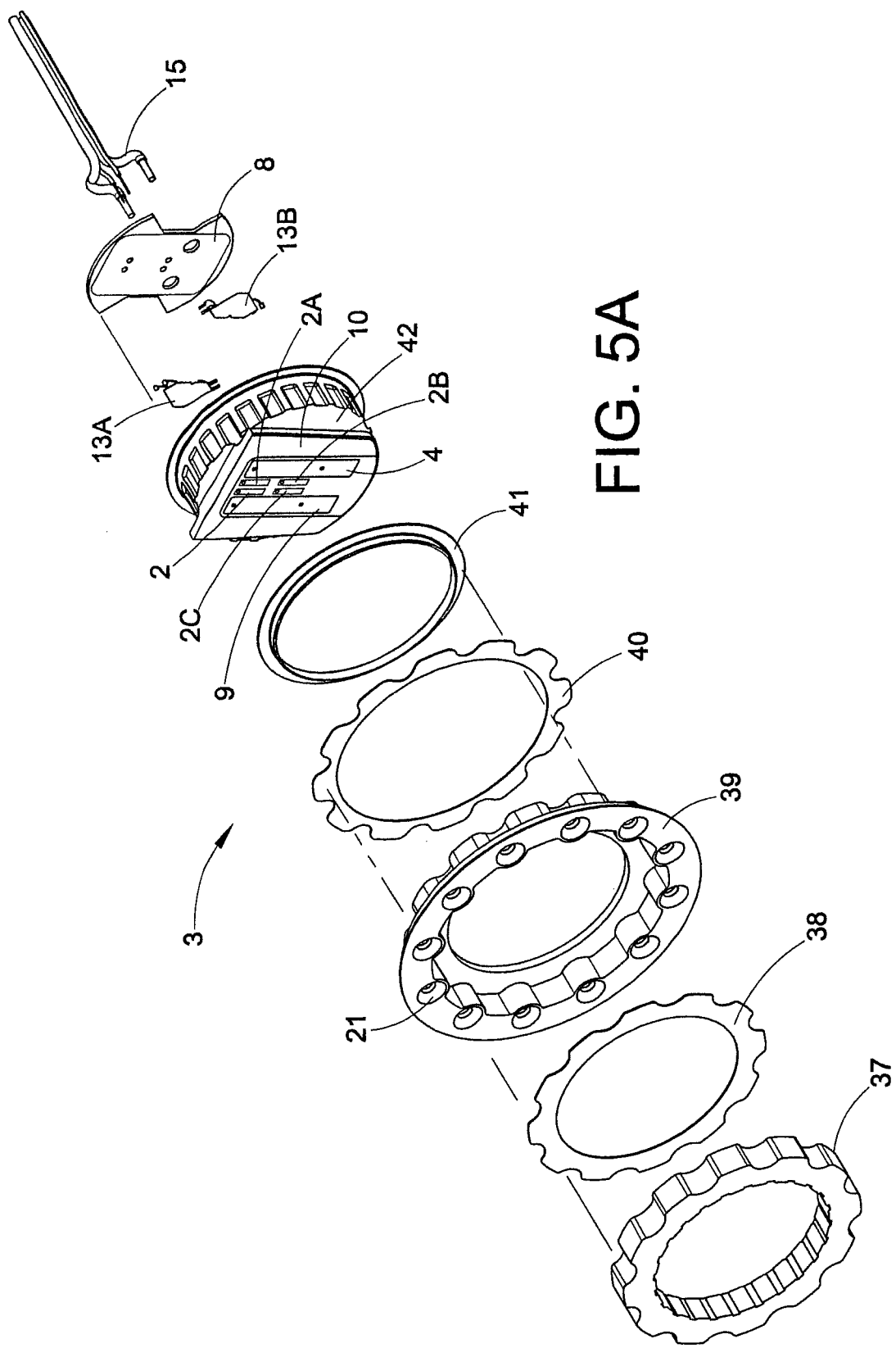
FIGS. 5A and 5B show exploded views of the male side of the connector of FIG. 2.
Figure 5B:
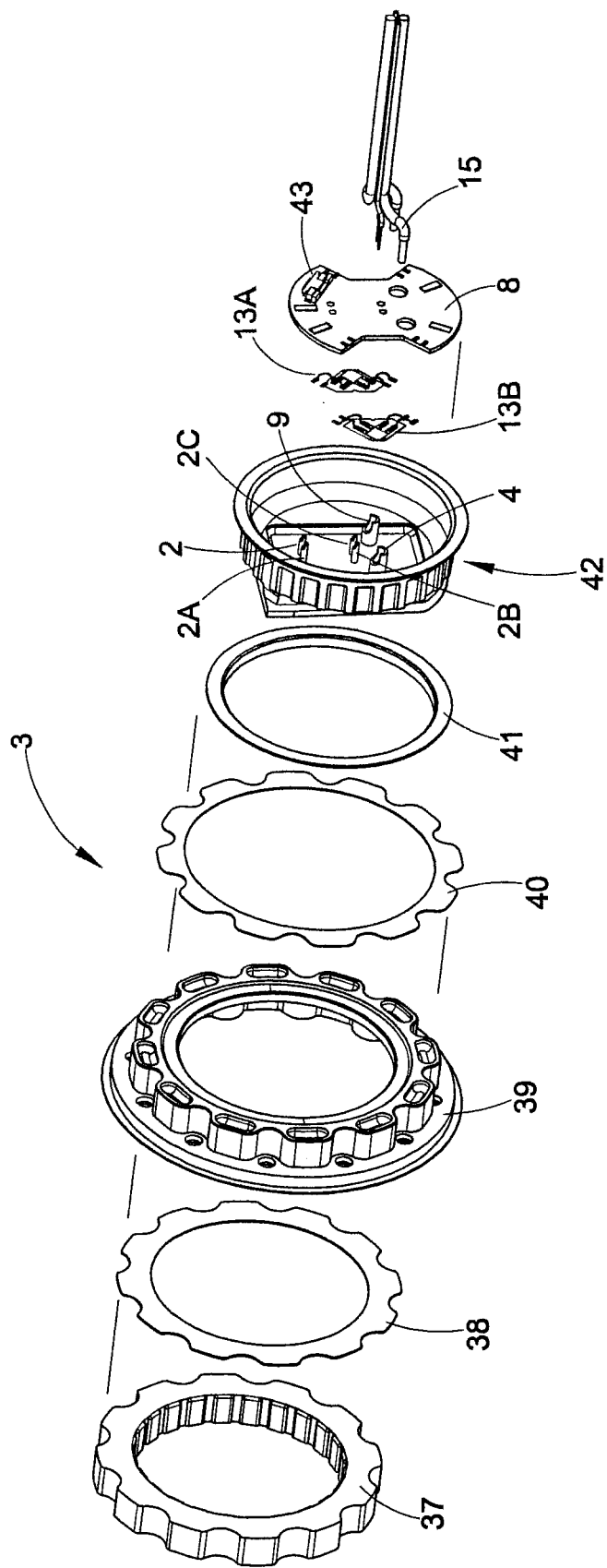

The male side connector/assembly 3, shown in exploded views in FIGS. 5A and 5B, can include a torsion member 37, a backing sheet 38, a shim 40, a connector side plain bearing 41, a drive support 39, a male joint connector subassembly 42, strain gages 13A and 13B for measurement of torque in the connector/joint, a connection printed circuit board 8, and internal wiring 15. A plurality of countersunk clearance holes 21 may be used to allow the male side assembly to be bolted to an artificial arm assembly or respective segment of the modular limb (see FIGS. 17-20).

Figure 6A:
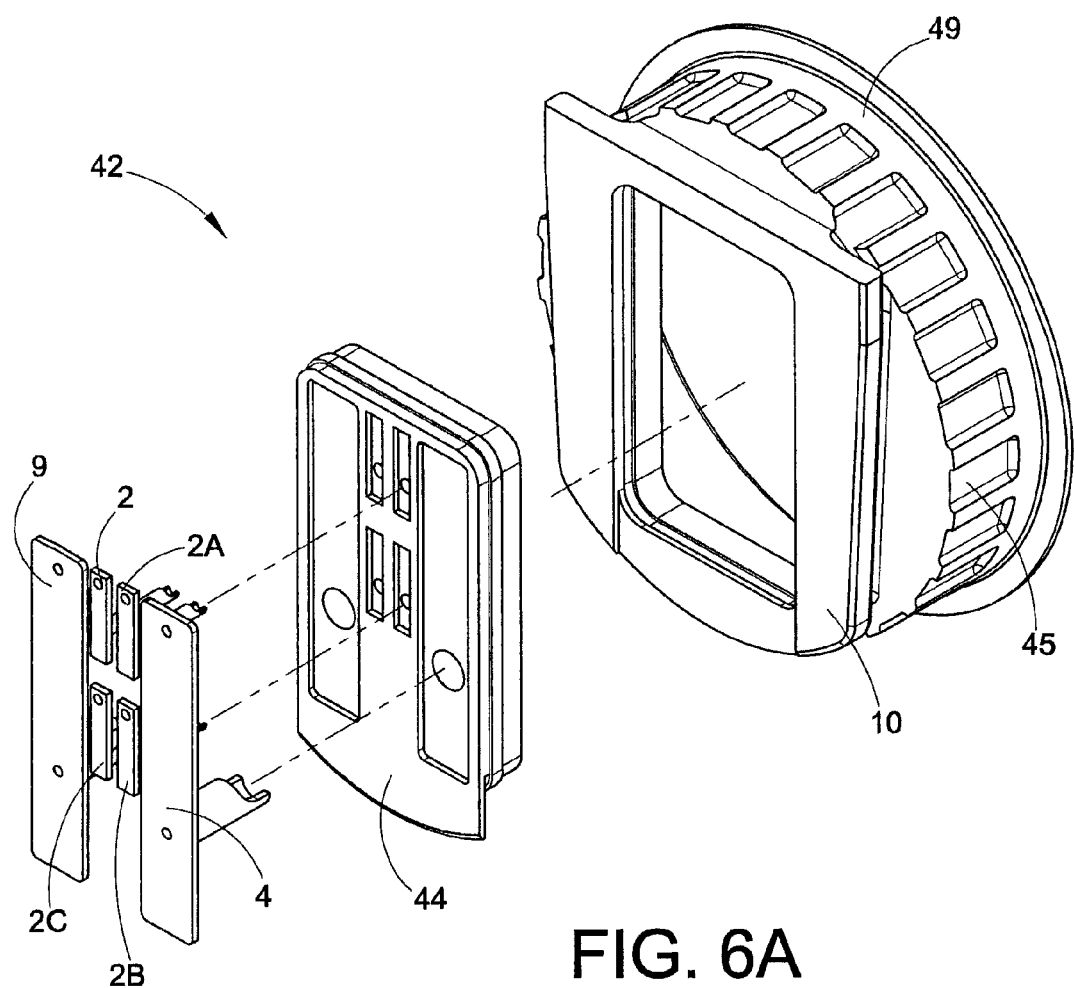
Figure 11:
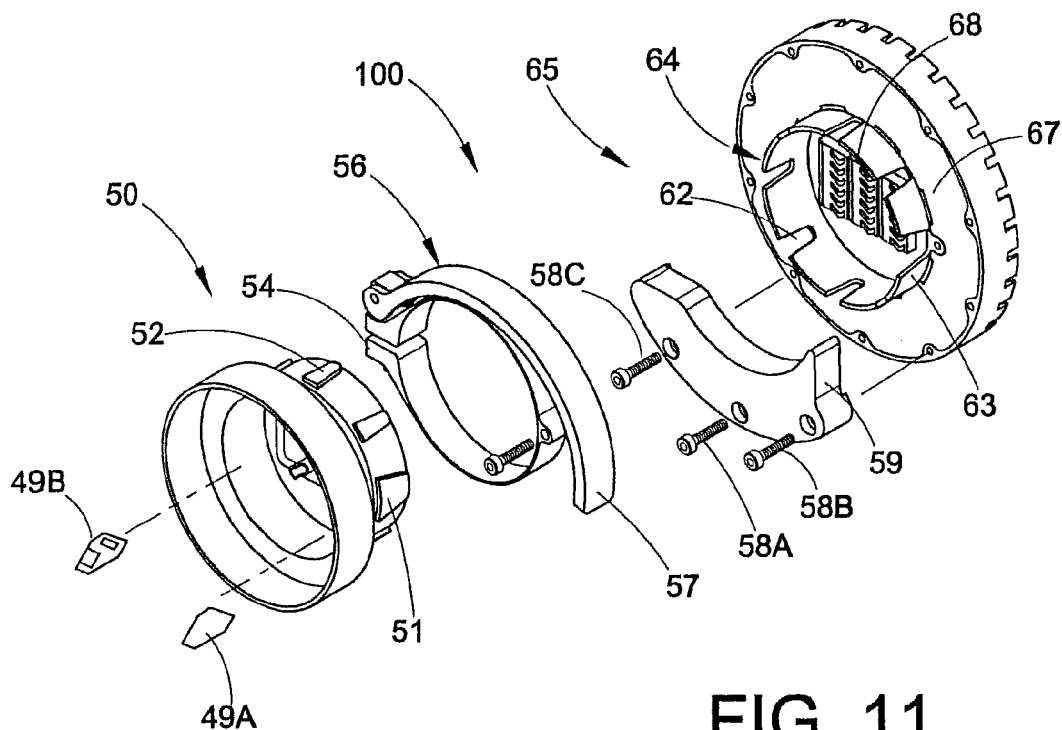
FIGS. 11 and 12 show exploded views of a connector assembly of FIG. 8.
Figure 12:
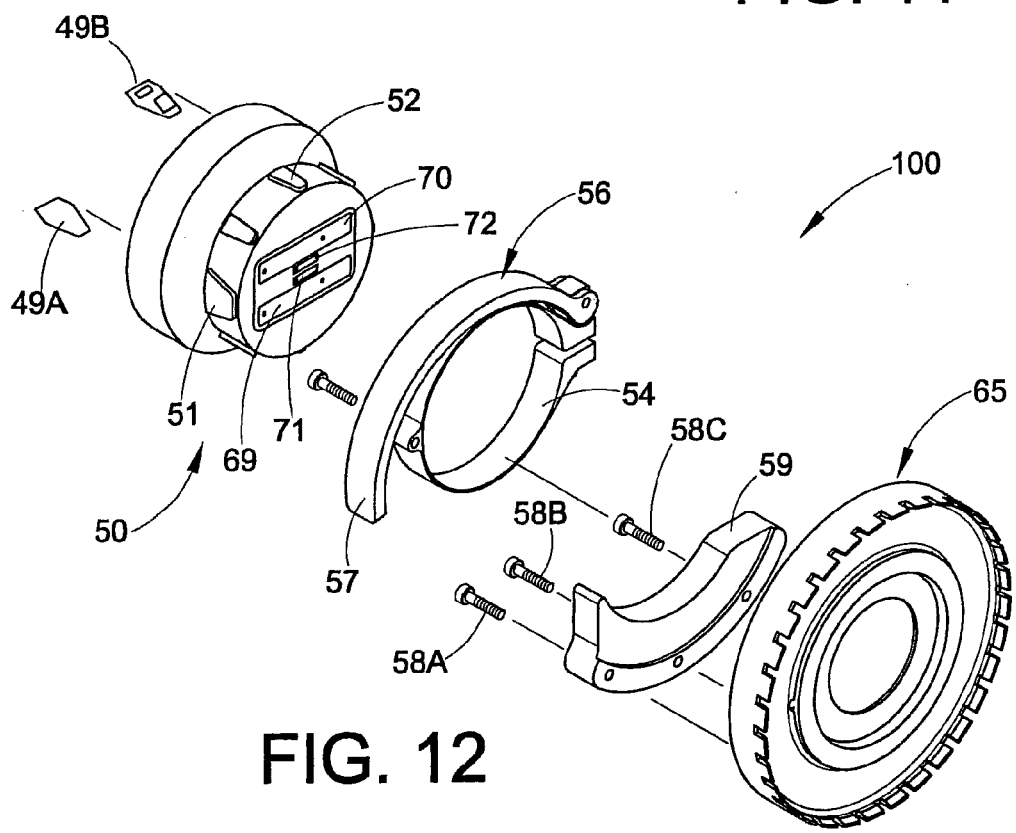

FIGS. 6A and 6B show exploded views of the male joint connector subassembly 42. In particular, the conductive power and ground contacts 4 and 9, the conductive communications bus contacts 2, 2A, 2B, and 2C, an electrically insulating connection plug 44, and the blade 10 (which may be made from hardened steel) are shown. In addition, knurling 45 can be formed on the housing 49 of the male joint connector subassembly 42 which increases the contact area with the toothed outer periphery of the polymer material of the torsion member 37. This helps improve the mechanical bond and prevent or retard the torsion member from slipping. It should be noted the torsion member can be a torsional spring manufactured from any material (plastic, rubber, metal, etc.) having the appropriate spring characteristics for the particular parameters (maximum load, stiffness, etc.) which the joint is designed to accommodate.

The locking clip assembly 11, shown in an exploded view in FIG. 7, includes a plain bearing 23, a lock or clip 46, and socket cap screws 19 and 19A. The plain bearing 23 (which can be made from a polymer based material) in this embodiment fits into recess 47 in lock 46 and the screws 19 and 19A fit into the counterbored clearance holes 48 and 48A.

Operation of the First Embodiment

Figure 17:
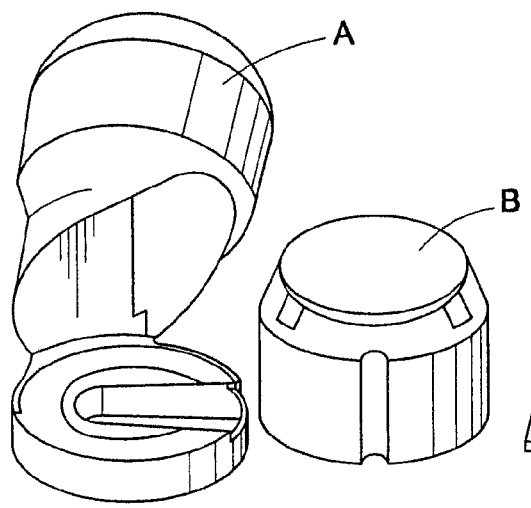
FIGS. 17-20 show the steps involved in securing a first limb element to a second limb element when employing the male side assembly and female side assembly illustrated in FIGS. 1A-7.
Figure 18:
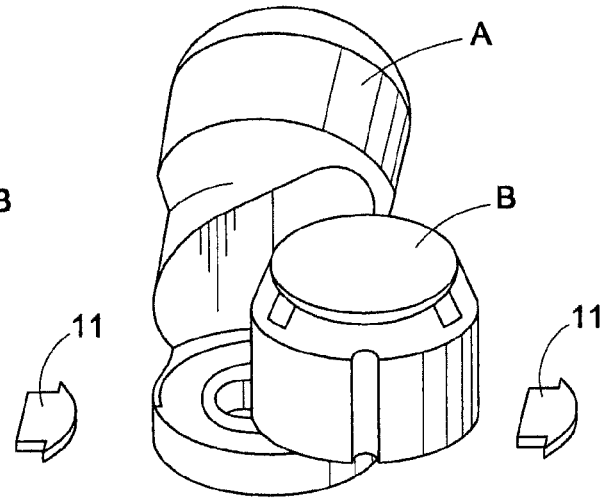
Figure 19:
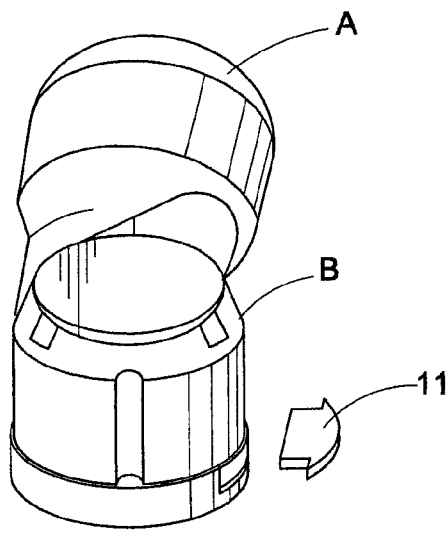

In operation, the male side connector/assembly 3 and female side connector/assembly 12 can be attached to separate artificial arm sections (e.g., see modules A and B as shown in FIGS. 17-20). These can be a humeral rotator and an elbow, as illustrated in FIGS. 17-20. However, they can, instead, be other limb segments of an arm or a leg or a robot. As is shown in FIG. 2, the joint connection process begins by first sliding blade 10 of male side connector 3 into the socket/receiver 29 of female side connector 12. The joint connection is fully established when blade 10 is fully engaged in a sliding interference fit with edge or lip 17 in receiver/socket 29. These steps are shown in FIGS. 17 and 19. When full engagement is achieved then power and ground contacts 4 and 9 are in intimate contact with the plurality of conductive spring pins 18, and communications contacts 2, 2A, 2B, and 2C are each in intimate contact with its respective spring pin 18.

Figure 20:
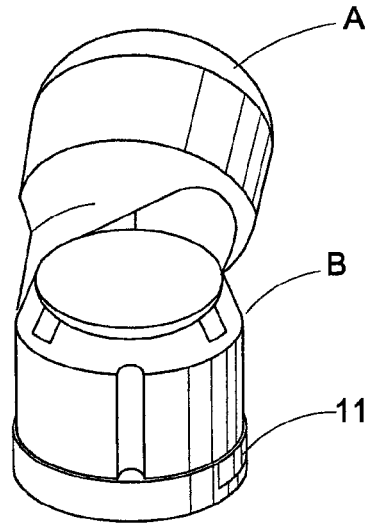

To ensure that the male side connector 3 and female side connector 12 do not become disengaged during service or operation, the locking clip assembly 11 is inserted into receiver 29 after blade 10 is fully engaged with edge/lip 17. In the embodiment shown, the screws 19 and 19A (see FIG. 7) are driven into threaded holes 31 (see FIGS. 4A-4B) and tightened. Of course, other ways of securing the locking clip in place, in a manner that the clip can be detached as needed when disassembling the joint, are also contemplated. The modular limb joint assembly 1 is thus configured as shown in FIGS. 1A and 1B. Similarly, FIG. 20 shows the two arm section modules in a connected fashion. In the embodiment shown, the first arm section can be the humeral rotator A and the second arm section can be an elbow B. However, other embodiments are also contemplated. In other words, the two limb sections which are joined can be, for example, a wrist connection to a forearm or an upper arm connection to a shoulder.

When the male and female connectors are fully engaged, blade 10 transfers rotational and linear mechanical loads from the male connector 3 to the socket/receiver 29 in the female connector 12. Electrical contacts 4, 9, 2, 2A, 2B, and 2C transfer power and electrical signals from the male connector 3 to spring pins 18 in the female connector 12.

Torsion member 37 and plain bearing 41 allow rotation of the male joint connector subassembly portion 42 in relation to the base/drive support 39. The rotation allowed by torsion member 37 reduces the torsional stiffness of the connector about the axis of torsion member 37 so that torsional shock loads transferred across the joint are minimized. The reduced stiffness allowed by torsion member 37 also allows better control of torque passing through the joint. In the embodiment illustrated, joint torque is measured by means of strain gages 13A and 13B mounted in male joint inner connector portion 42. It should be noted that the strain gages or other load, torque, or position sensing devices can be located in either or both of the male and female side connectors.

Detailed Description of the Second Embodiment

Another embodiment of the joint assembly 100 is shown in FIGS. 8 through 16. As is shown in the drawings and particularly in FIG. 10, the joint assembly 100 has a male side connector 50 which slides into a female side connector 65. In this embodiment, a sliding motion along the aligned axes of the male side connector 50 and the female side connector 65 is contemplated. A locking lever assembly 56 secures together the two associated limb segments attached to the respective male/female side connectors of the joint assembly.

When fully assembled as shown in FIG. 8 the joint assembly 100 forms a compact joint that provides robust mechanical attachment, multiple weather-sealed electrical connections, and integral torque sensing. As is shown in particular in FIGS. 9-12, the mechanical attachment between female side connector 65 and male side connector 50 is achieved when a plurality of tabs 52 on a hub portion 74b of the male side connector slide into a plurality of slots or notches 62 in the socket/receiver of the female connector. Moreover, an indexing tab 51 slides into an indexing slot 63 in the female receiver 64 in order to correctly orient the male side assembly in relation to the female side assembly. Naturally, the tabs, slots, or notches can be arranged in any configuration and on either connector so as to facilitate positive traction or engagement between the male and female connectors of the joint for the purpose of transmitting torsional as well as axial loads. Electrical contact/communication can be achieved through flat contacts 69, 70, 71, and 72 in male side connector 50 when such contacts engage a plurality of spring pins 68 in the female side connector 65.

Figure 13:
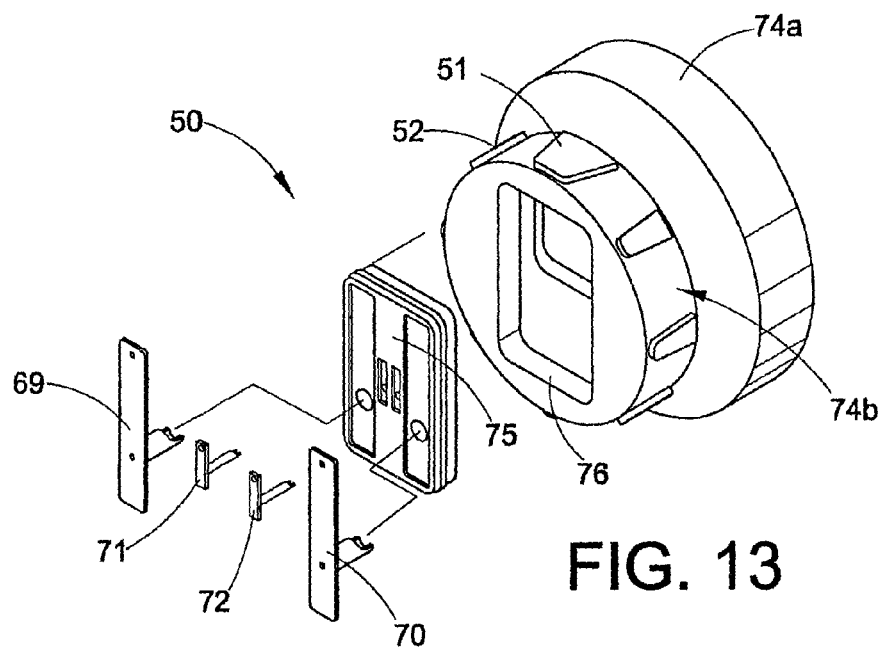
FIG. 13 shows an exploded view of the male side of the connector of FIG. 8.

The male side connector 50 is shown in an exploded view in FIG. 13. In general, the male connector 50 may include a cup or base portion 74a, the load bearing hub or projection 74b, a connection plug 75, a plug recess 76, and electrical contacts 69, 70, 71, and 72. As with the first embodiment, torque about the cylindrical axis (or axis of rotation) of the joint assembly can be measured by means of strain gauges 49A and 49B mounted to the male connector 50 (as illustrated) or to the female connector 65.

Figure 14:
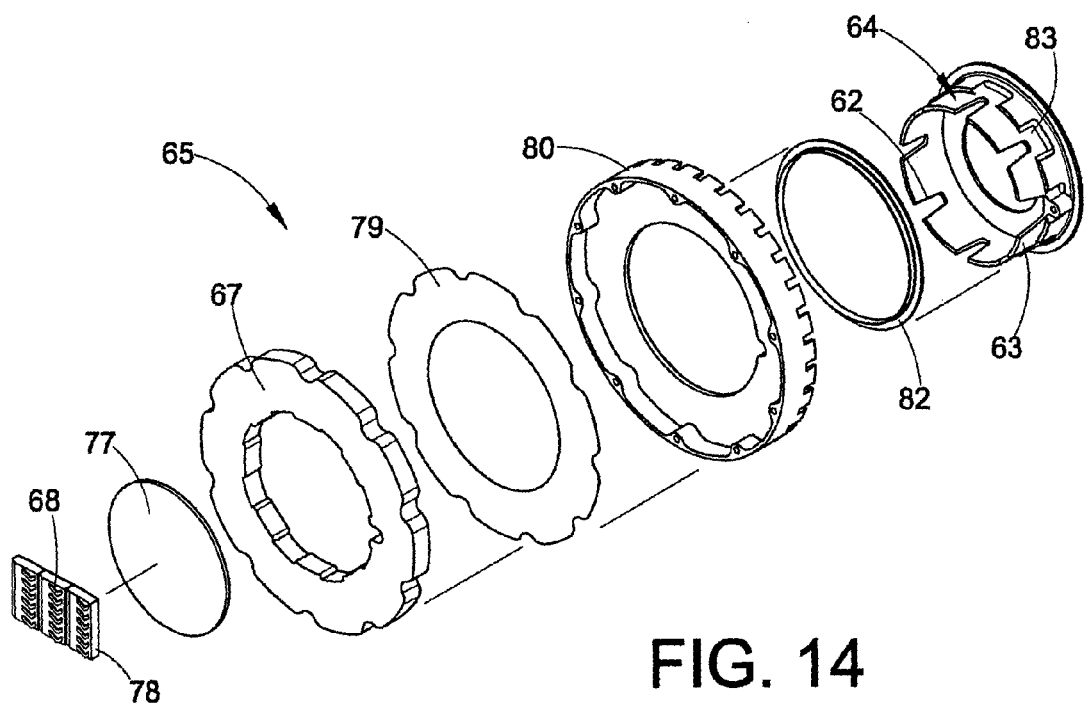
FIGS. 14 and 15 show exploded views of the female side of the connector of FIG. 8.
Figure 15:
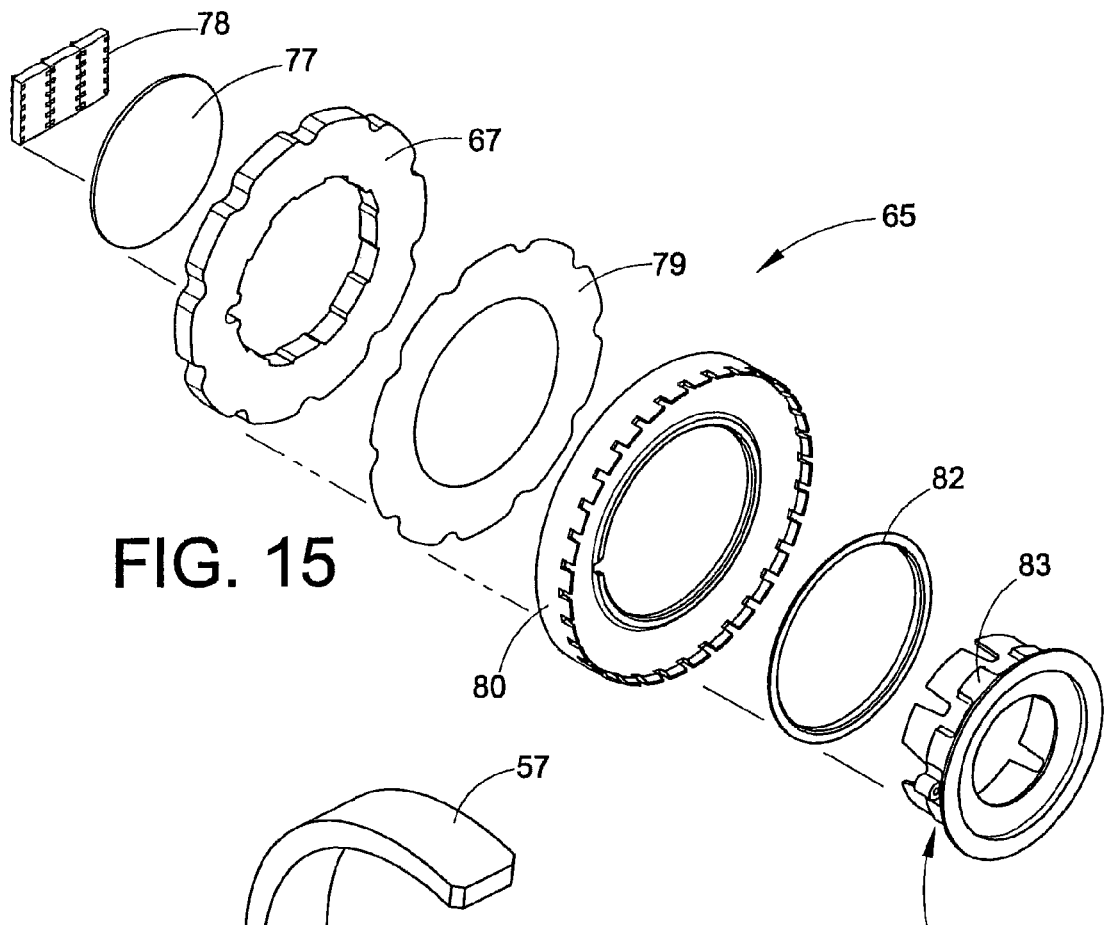

As is shown in the exploded views in FIGS. 14 and 15, the female side connector 65 may include a spring pin mounting circuit board 77, electrical spring pins 68 in spring pin blocks 78, a torsional member 67, a backing sheet 79, a housing 80, a plain bearing 82, and a female receiver or socket 64. Power and ground contacts 69 and 70 (FIG. 13) can each be contacted by multiple spring pins 68 to allow high electrical currents to flow across the joint assembly. In addition, knurling 83 can also be formed on the body of the socket 49 of the female joint connector 65 which increases the contact area with the toothed inner periphery of the torsion member 67. Similarly, as best illustrated in FIG. 14, the housing 80 can be knurled or toothed so as to mesh with a toothed outer periphery of the torsion member 67. This helps improve the mechanical bond and prevent or retard slipping between the torsion member and the male and/or female joint connectors.

Figure 16:
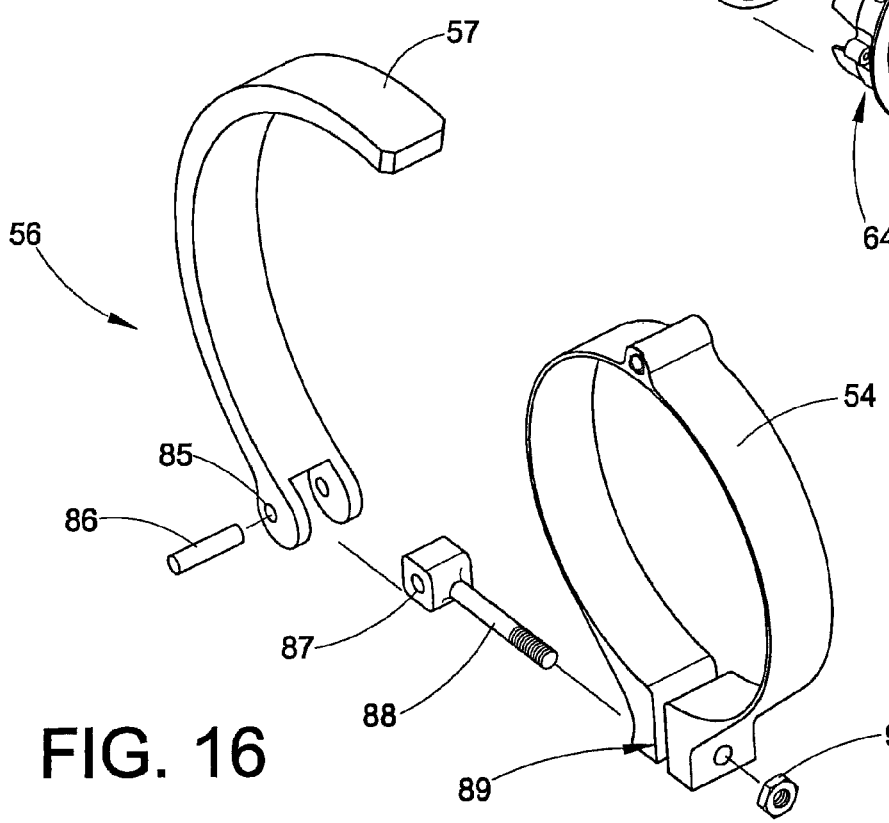
FIG. 16 shows an exploded view of a locking lever assembly of the connector of FIG. 8.

The locking lever assembly 56, shown in an exploded view in FIG. 16, can be composed of a locking collar 54, a locking lever 57, a pin 86, a pull rod 88, and a nut 91. A head portion 87 of the pull rod 88 is pivotally secured in a lobed end 85 of the lever 57 by the pin 86. Rotating the lever 57 causes a split 89 in the collar 54 to open or close, depending on the direction of rotation. In this manner, when the lever assembly 56 is placed in a locked state, it cinches the socket/receiver of the female connector about the hub portion of the male connector creating a rigid joint connection. In addition, a locking lever guard 59 (FIGS. 11-12) may also be provided and secured to the housing 80 by way of fasteners 58A-58C. It should be appreciated that other locking lever assembly constructions can also be employed.

Operation of the Second Embodiment

In operation, the male side connector 50 and female side connector 65 are attached to separate limb segments or modules (not shown for this embodiment) that are to be joined together using the previously described joint assembly. In one embodiment, these can be a wrist and a forearm, for example. As is shown in FIG. 10, the joint is established by first sliding the tabs 52 of male connector 50 into slots 62 of the socket/receiver 64 of female connector 65 (with the male and female sides oriented so that indexing tab 51 engages indexing slot 63). The male and female connectors are fully engaged when tabs 52 and 51 bottom in slots 62 and 63 of the receiver 64. When full engagement is achieved, power and ground contacts 69 and 70 are in intimate contact with a plurality of conductive spring pins 68, and communications contacts 71 and 72 are each in intimate contact with a single spring pin 68.

To ensure that the male connector 50 and female connector 65 do not become disengaged during operation of the artificial, prosthetic, or robotic limb, locking lever 57 (shown opened in FIG. 9) is pushed down into the position shown in FIG. 8 to clamp female socket/receiver 64 around hub portion 74b (FIG. 13). The joint is thus established as shown in FIG. 8.

When the joint is fully established, tabs 52 and 51 transfer torque to slots/notches 62 and 63 in socket/receiver 64 in the female side assembly 65. Electrical contacts 69, 70, 71, and 72 transfer electrical power and electrical signals from the male connector 50 to spring pins 68 in the female connector 65 thus establishing electrical communication between the limb segments of the artificial limb.

Torsion member 67 and plain bearing 82 allow rotation of female receiver/socket 64 with respect to housing/base 80 about the cylindrical axis of housing 80. The rotation allowed by torsion member 67 reduces the torsional stiffness of the connector about the axis of spring 67 so that torsional shock loads transferred across the joint are minimized. The reduced stiffness allowed by torsion member 67 also facilitates better control of torque passing through the joint. Torque in the joint can be measured by means of strain gages 49A and 49B mounted to the male connector 50. As discussed with respect to the first embodiment, other known means for measuring torque are also contemplated.

The modular limb joint assembly disclosed herein can be used to connect multiple modules or segments of an associated modular limb in series. It provides a high strength mechanical connection capable of bearing high torque and axial loads, as well as an integral electrical connection for power and signals. It also includes integral torque sensing elements. Further, it the torsion member 67 provides an elastic element, compliance element, or torsion member which enables some resiliency in the joint. It should be noted that the torsion member 67 may also serve as a series elastic element within the joint assembly which is effectively in series between the "input" or driving end of the joint and the "output" or driven end of the joint. Such a series elastic element may act as low pass filter effectively filtering out shock loads while providing enhanced force control and stability (particularly when coupled with load or torque sensors as described previously). A more detailed discussion of the advantages of using a series elastic element can be found in U.S. Pat. No. 5,910,720 to Williamson, et al. (Williamson '720), the entire disclosure of which is incorporated herein by reference. As described at col. 3, line 61-col. 4, line 27 of Williamson '720 in the context of a motor driving a load through a gearbox, the series elastic element acts as a low pass filter to shock loads, thereby protecting the gearbox and motor from damage. At col. 4, lines 35-47, Williamson '720 further states that:

> . . . the torsional spring element . . . may be constructed of, e.g., steel, aluminum, delrin, or nylon 66, or other suitable material. Preferably, the spring is an integral structure that is light-weight and compact, and exhibits a desired stiffness for a given application. Note that the spring actually carries the actuator load; as a result, the spring optimally is of a high loadcarrying capacity, or at least a carrying capacity suitable for a given load application. In addition, it is preferable that the spring exhibit no hysterisis, i.e., no energy loss per compression cycle, and that the spring be of a geometry that is easy to attach between the actuator driving mechanism and the actuator load element.

Typical artificial limbs, such as prosthetic arms or robot arms, are designed as a single integrated assembly which cannot be simply and quickly disassembled into component modules. Moreover, such arms are not designed with load and/or torque sensing elements which are integral to the connector, since they do not even have a modular connector. Due to the lack of easily connectible limb modules or segments, typical man-made arms do not have a single assembly which combines the mechanical and electrical interface with a load and/or torque sensor, as well as a compliance element, as in the disclosed embodiments.

Disclosed has been a new and improved artificial limb, such as an arm, which comprises modular segments. With the system disclosed herein, the reliability and safety of the electrical connection can be improved. At the same time, an integral torque sensor can be provided along with a compliance or torsion element to allow the joint between two segments of a limb to function better.

According to one embodiment of the present disclosure, there is provided a connecting device which electrically connects first and second components of an artificial limb. The connecting device comprises a first component block including a blade and a second component block including a socket in which the blade is selectively accommodated. A locking clip can selectively secure the first component block to the second component block.

According to another embodiment of the present disclosure, a joint is provided for an artificial limb. The joint comprises a first connector including a blade and a first electrical contact surface and a second connector including a socket in which the blade is selectively accommodated, the socket including a second electrical contact surface. A locking clip is provided for securing the first connector to the second connector. Electrical communication is achieved between the first and second connectors when the first and second electrical contact surfaces are in contact with each other.

The disclosure has been described with reference to several embodiments. Obviously, alterations and modifications will occur to others upon a reading and understanding of this specification. It is intended to include all such modifications and alterations insofar as they come within the scope of the appended claims or the equivalents thereof.

What is claimed is:

1. A joint assembly for releasably securing a first and a second segment of an associated modular limb, the joint assembly comprising:
    a male connector including a base, a load bearing hub secured to the base of the male connector, and at least one first electrical contact secured to the load bearing hub, the base of the male connector being adapted to be secured to one of the first and second segments of the associated modular limb;
    a female connector including a base, a load bearing socket secured to the base of the female connector, and at least one second electrical contact secured to the female connector and located in the load bearing socket, the load bearing hub of the male connector being engaged with and coupled to the load bearing socket of the female connector to transmit torque between the hub and socket, the base of the female connector being adapted to be secured to the other of the first and second segments of the associated modular limb;
    wherein the at least one first electrical contact is aligned with and in contact with the at least one second electrical contact when the hub is received in the socket for establishing electrical communication between the first and second segments of the associated modular limb;
    said female connector comprising a resilient series elastic element that is ring shaped and disposed between and adapted for transmitting torque between the socket of the female connector and the base of the female connector, the series elastic element adapted to resiliently absorb shock loads between the socket of the female connector and the base of the female connector such that the male connector and the female connector cooperate to form a resilient yet releasable modular limb joint, wherein said series elastic element comprises a toothed outer periphery engaged with a complimentary toothed portion of the base of the female connector and comprises an inner periphery engaged with the socket of the female connector to resiliently couple said base and socket of said female connector.

2. The joint assembly of claim 1, further comprising a locking member for selectively securing the load bearing hub of the male connector to the socket of the female connector, wherein the load bearing hub is rigidly coupled to the socket when the locking member is in a locked state.

3. The joint assembly of claim 2, wherein said locking member comprises a collar that cinches said socket about said hub when said collar is in its locked state to rigidly couple said hub to said socket.

4. The joint assembly of claim 3, further comprising a lever operably coupled to said collar and selectively movable to a locked position to place said collar in said locked state.

5. The joint assembly of claim 1, wherein the hub includes one of a plurality of tabs or notches and the socket includes the other of the plurality of tabs or notches, the plurality of tabs and the plurality of notches being aligned when the hub is received into the socket for transmitting torque between the hub and the socket.

6. The joint assembly of claim 1, wherein one of the male connector and the female connector includes a load sensor for measuring a torsional load across the joint.

7. The joint assembly of claim 6, wherein the load sensor comprises one of a full, half, or quarter strain gage bridge connected to said one of said male connector and said female connector.

8. The joint assembly of claim 7, wherein the strain gage bridge includes a first half and a second half, the first half of the bridge being disposed adjacent the hub of the male connector at a first location spaced from an axis of rotation of the joint and the second half of the bridge being disposed adjacent the hub of the male connector at a second location spaced from the axis of rotation of the joint.

9. The joint assembly of claim 1, wherein the engagement of the load-bearing hub in the load-bearing socket provides a weathertight seal for the at least one first electrical contact and the at least one second electrical contact.

10. A joint assembly for releasably securing a first and a second segment of an associated modular limb, the joint assembly comprising:
    a male connector including a base, a load bearing hub secured to the base of the male connector, and at least one first electrical contact secured to the load bearing hub, the base of the male connector being adapted to be secured to one of the first and second segments of the associated modular limb;
    a female connector including a base, a load bearing socket secured to the base of the female connector, and at least one second electrical contact secured to the female connector, the base of the female connector being adapted to be secured to the other of the first and second segments of the associated modular limb;
    said load bearing hub engaged with and coupled to the load-bearing socket for transmitting torque between the male and female connectors;
    wherein the at least one first electrical contact is aligned and in contact with the at least one second electrical contact when the hub is engaged with the socket for establishing electrical communication between the first and second segments of the associated modular limb;
    a resilient torsion member located in the joint assembly between the socket of the female connector and the base of the female connector such that the resilient torsion member provides a series elastic element that is adapted to resiliently filter shock loads between the socket of the female connector and the base of the female connector, wherein said resilient torsion member comprises a toothed outer periphery engaged with a complimentary toothed portion of the base of the female connector and comprises an inner periphery engaged with the socket of the female connector to resiliently couple said base and socket of said female connector.

11. The joint assembly of claim 10, further comprising a locking member for selectively rigidly securing the hub to the socket when the locking member is in a locked state.

12. The joint assembly of claim 11, wherein said locking member comprises a collar that cinches said socket about said hub when said collar is in its locked state to rigidly couple said hub to said socket.

13. The joint assembly of claim 12, further comprising a lever operably coupled to said collar and selectively movable to a locked position to place said collar in said locked state.

14. The joint assembly of claim 10, wherein the hub includes one of a plurality of tabs or notches and the socket includes the other of the plurality of tabs or notches, the plurality of tabs and the plurality of notches being aligned when the hub is received into the socket for transmitting torque between the hub and the socket.

15. The joint assembly of claim 10, wherein one of the male connector and the female connector includes a load sensor for measuring a torsional load across the joint.

16. The joint assembly of claim 15, wherein the load sensor comprises one of a full, half, or quarter strain gage bridge.

17. The joint assembly of claim 16, wherein the strain gage bridge includes a first half and a second half, the first half of the bridge being disposed adjacent the hub at a first location spaced from an axis of rotation of the joint and the second half of the bridge being disposed adjacent the hub at a second location spaced from the axis of rotation of the joint.

18. The joint assembly of claim 10, wherein the male connector and the female connector form a weathertight seal enclosing the at least one first electrical contact and the at least one second electrical contact.

19. A joint assembly for releasably securing a first and a second segment of an associated modular limb, the joint assembly comprising:

a male connector including a base, a load bearing hub secured to the base of the male connector, and a first electrical contact secured to the load bearing hub, the base of the male connector being adapted to be secured to one of the first and second segments of the associated modular limb;

a female connector including a base, a load bearing socket secured to the base of the female connector, and a second electrical contact secured to the female connector, the base of the female connector being adapted to be secured to the other of the first and second segments of the associated modular limb;

said load bearing hub engaged with and coupled to the load-bearing socket for transmitting torque between the male and female connectors, said first electrical contact contacting the second electrical contact when the hub is engaged with and coupled to the socket for establishing electrical communication between the first and second segments of the associated modular limb;

a torsion spring located in the joint assembly for reducing torsional stiffness and filtering shock loads between the male connector and the female connector such that said male connector and female connector cooperate to form a resilient and releasable modular limb joint, said torsion spring located between and engaged with both said base and socket of the female connector and comprising a toothed outer periphery engaged with a complimentary toothed portion of the base of the female connector to resiliently couple said base and socket of said female connector.

* * * * *